United States Patent
Lovett et al.

(10) Patent No.: US 8,734,499 B2
(45) Date of Patent: May 27, 2014

(54) SYSTEMS AND METHODS FOR THERMAL NEUROINHIBITION

(75) Inventors: Eric G. Lovett, Mendota Heights, MN (US); Imad Libbus, St. Paul, MN (US); Joseph Walker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1909 days.

(21) Appl. No.: 11/693,001

(22) Filed: Mar. 29, 2007

(65) Prior Publication Data

US 2008/0243212 A1 Oct. 2, 2008

(51) Int. Cl.
*A61F 7/12* (2006.01)

(52) U.S. Cl.
USPC ............................ 607/105; 607/96; 607/113

(58) Field of Classification Search
USPC .................................................. 607/96, 105
See application file for complete search history.

(56) References Cited

U.S. PATENT DOCUMENTS

| | | | |
|---|---|---|---|
| 4,207,897 A | 6/1980 | Lloyd et al. | |
| 6,248,126 B1 * | 6/2001 | Lesser et al. | 607/113 |
| 6,364,899 B1 * | 4/2002 | Dobak, III | 607/113 |
| 6,393,323 B1 * | 5/2002 | Sawan et al. | 607/41 |
| 6,882,881 B1 | 4/2005 | Lesser et al. | |
| 7,200,504 B1 * | 4/2007 | Fister | 702/75 |
| 7,232,458 B2 * | 6/2007 | Saadat | 607/105 |
| 7,277,761 B2 | 10/2007 | Shelchuk | |
| 7,500,985 B2 * | 3/2009 | Saadat | 607/105 |
| 2002/0068964 A1 * | 6/2002 | Dobak, III | 607/105 |
| 2002/0111657 A1 * | 8/2002 | Dae et al. | 607/113 |
| 2003/0225442 A1 | 12/2003 | Saadat | |
| 2004/0133120 A1 * | 7/2004 | Frei et al. | 600/544 |
| 2004/0133248 A1 * | 7/2004 | Frei et al. | 607/45 |
| 2004/0210286 A1 * | 10/2004 | Saadat | 607/105 |
| 2005/0171585 A1 * | 8/2005 | Saadat | 607/96 |
| 2005/0205241 A1 | 9/2005 | Goodson et al. | |
| 2005/0224086 A1 | 10/2005 | Nahon | |
| 2006/0229688 A1 * | 10/2006 | McClure et al. | 607/72 |
| 2009/0149919 A1 * | 6/2009 | Dacey et al. | 607/62 |
| 2009/0149926 A1 * | 6/2009 | Dacey et al. | 607/96 |

FOREIGN PATENT DOCUMENTS

WO WO-99/34758 A1 7/1999
WO WO-2008/121231 A2 10/2008

OTHER PUBLICATIONS

"Application Serial No. PCT/US2008/003545, International Search Report mailed Nov. 3, 2008", 3 pgs.
"Application Serial No. PCT/US2008/003545, Written Opinion mailed Nov. 3, 2008", 6 pgs.

(Continued)

*Primary Examiner* — Linda Dvorak
*Assistant Examiner* — Kaitlyn Smith
(74) *Attorney, Agent, or Firm* — Schwegman Lundberg & Woessner, P.A.

(57) ABSTRACT

Disclosed herein, among other things, is system for thermal neuroinhibition. According to an embodiment, the system includes at least one implantable fluid-filled conduit adapted to be placed adjacent to a neural target. The system also includes an implantable housing including a power source, a heat pump deriving power from the source and connected to the conduit, and a controller within the housing. The controller is connected to the heat pump, and is adapted to control the heat pump to effect fluid flow in the conduit to cool the neural target using electromechanical refrigeration to reversibly inhibit neural activity as part of a medical treatment.

19 Claims, 5 Drawing Sheets

(56) References Cited

OTHER PUBLICATIONS

"High Energy Density Rechargeable Li-Ion Batteries", [online]. [retrieved Nov. 15, 2006]. Retrieved from the Internet: <URL: http://sbir.gsfc.nasa.gov/SBIR/successes/ ss/7-015text.html>, 1 pg.

"Research and Development of micro heat exchangers", [online]. [retrieved Nov. 15, 2006]. Retrieved from the Internet: <URL: http://www.hee.k.u-tokyo.ac.jp/research/MHex-e.html>, 2 pgs.

Ackerman, M. J., et al., "Ion Channels—Basic Science and Clinical Disease", *N Engl J Med.*, 336(22), (1997), 1575-1586.

Borgdorff, P., et al., "An Implantable Nerve Cooler for the Exercising Dog", *Eur J Appl Physiol Occup Physiol.*, 53(2), (1984), 175-179.

Drost, M. K., et al., "Recent Developments in Microtechnology-Based Chemical Heat Pumps", [online]. Retrieved from the Internet: <URL:http://www.pnl.gov/microcats/aboutus/publications/microchemical/dechema99.pdf>, U.S. Department of Energy, Pacific Nothwest National Laboratory, (1999), 21 pgs.

Potter, E. K., et al., "Potentiation of Cardiac Vagal Action by Cold.", *Clinical Science,* 68(2), (1985),165-169.

Stone, H. L., et al., "Ventricular Output in Conscious Dogs Following Acute Vagal Blockade", *J Appl Physiol.*, 24(6), (1968), 782-786.

Versteeg, P. G., et al., "Influence of Vagal Cooling on Cardiac Output in Normal and Beta-Blocked Exercising Dogs", *European Journal of Applied Physiology and Occupational Physiology*, 54(6), (1986), 617-623.

Wegeng, R., et al., "Micro Chemical System Development Progress at the Pacific Northwest National Laboratory", [online]. Retrieved from the Internet: <URL: http://www.pnl.gov/microcats/aboutus/publications/microchemicalsystemdevelopment.pdf>, (1997), 1-8.

\* cited by examiner

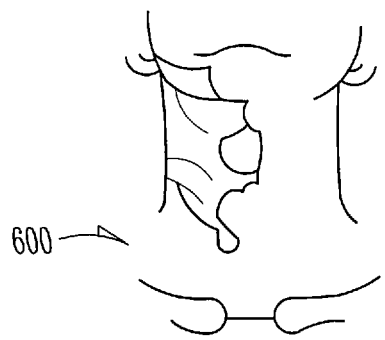 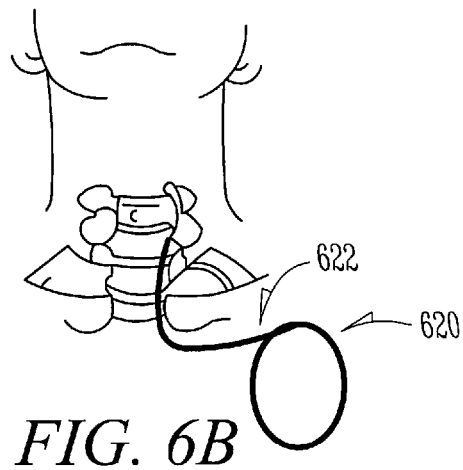
FIG. 6A    FIG. 6B
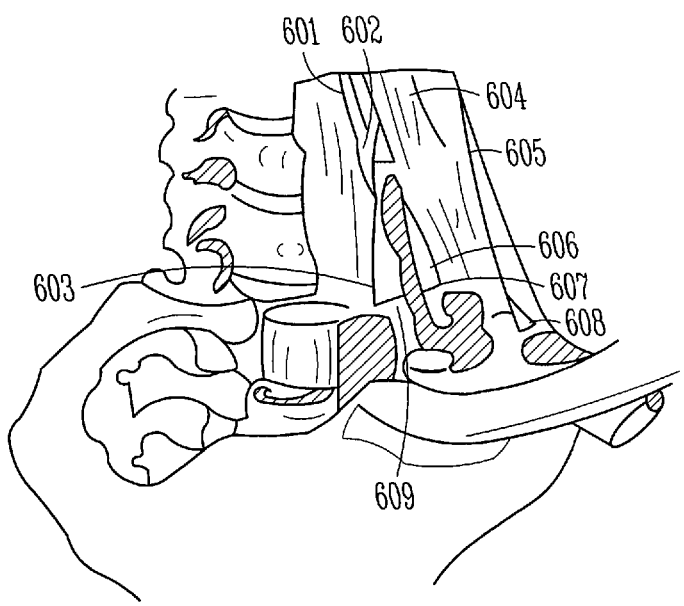
FIG. 6C

SYSTEMS AND METHODS FOR THERMAL NEUROINHIBITION

TECHNICAL FIELD

This disclosure relates generally to medical devices, and more particularly systems and methods for thermal neuroinhibition.

BACKGROUND

A number of therapies involve neural stimulation, including the stimulation or inhibition of nerve traffic in motor and autonomic nerves. A sympathetic response can be achieved by inhibiting nerve traffic in a parasympathetic nerve target. A parasympathetic response can be achieved by inhibiting nerve traffic in a sympathetic nerve target. Inhibiting parasympathetic nerve traffic, for example, would serve to reduce the impact of the parasympathetic nervous system on an autonomically-regulated function and thereby increase sympathetic influences, either directly through reduction in parasympathetic activity or indirectly through reduction in reciprocal inhibition. Examples of neural stimulation (or neurostimulation) therapies include neural stimulation therapies for respiratory problems such as sleep disordered breathing, blood pressure control such as to treat hypertension, cardiac rhythm management, myocardial infarction and ischemia, heart failure, epilepsy, depression, pain, migraines, eating disorders and obesity, and movement disorders.

Improved systems and methods for controlling neural traffic are needed.

SUMMARY

Disclosed herein, among other things, is a system for thermal neuroinhibition. According to one embodiment, the system includes at least one implantable fluid-filled conduit adapted to be placed adjacent to a neural target. The system also includes an implantable housing including a power source, a heat pump deriving power from the source, the heat pump connected to the conduit, and a controller within the housing. The controller is connected to the heat pump, and is adapted to control the heat pump to effect fluid flow in the conduit to cool the neural target using electromechanical refrigeration to reversibly inhibit neural activity as part of a medical treatment.

Disclosed herein, among other things, is an implantable lead for use in a thermal neuroinhibition system. According to one embodiment, the lead includes at least one implantable fluid-filled conduit along the length of the lead. Thermal insulation is around at least a portion of the lead. The proximal end of the lead is adapted to connect to a device having at least one heat pump. The distal end of the lead is adapted to be placed adjacent a neural target. The distal end includes an uninsulated portion of the conduit adapted to cool the neural target using electromechanical refrigeration to reversibly inhibit neural activity as part of a medical treatment. In various embodiments, one or more sensors are included at the distal end, and the sensors are used in a closed loop feedback thermal neuroinhibition system.

Disclosed herein, among other things, is a method for applying thermal neuroinhibition treatment. According to an embodiment, the method includes identifying a patient as a candidate for neural inhibition. The method also includes operating an implantable heat pump to move fluid through a conduit past a neural target to cool the target and inhibit neural activity. In various embodiments, the method also includes sensing a physiological parameter and adjusting the cooling of the neural target based on the sensed physiological parameter.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

FIGS. 6A-6C illustrate a neural target for applying thermal neuroinhibition treatment, according to various embodiments.

DETAILED DESCRIPTION

Figure 1:
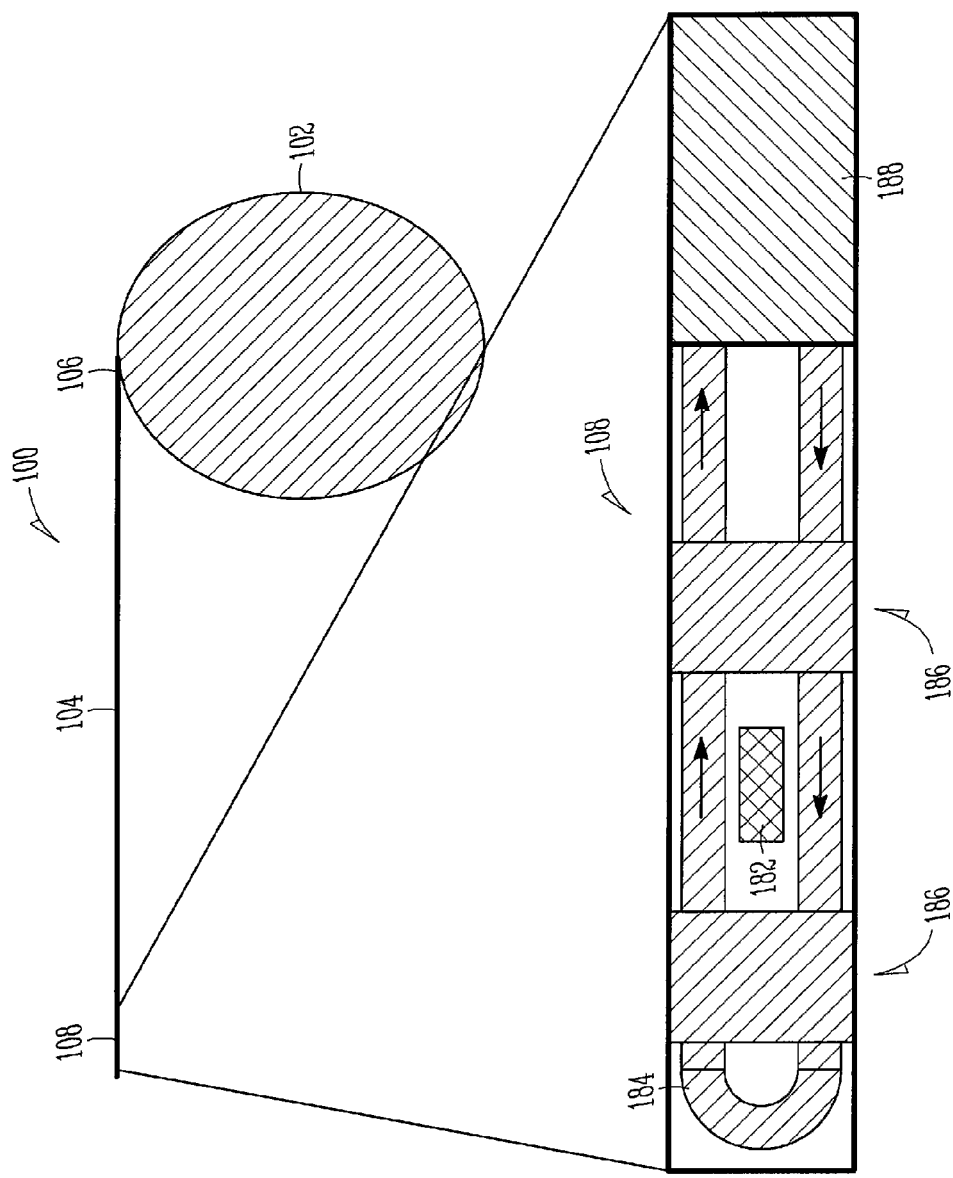
FIG. 1 illustrates a block diagram of a thermal neuroinhibition system, according to various embodiments.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter are related to thermal neuroinhibition treatment systems. The treatment systems can provide prophylactic treatments or therapeutic treatments. In various embodiments an implantable medical device (IMD) employs localized cooling to suppress or inhibit neural traffic. In various embodiments, a small, implanted heat pump in the IMD is used to remove heat from a neural target to modulate nerve conduction. Heat transfer is achieved by placing a fluid-filled conduit adjacent to or in contact with a neural target, in various embodiments. For example, the IMD can be used to control sensation and motor activity. Other applications include, but are not limited to pain control, regulation of the cardiovascular system, control of incontinence, and modulation of gastrointestinal motility. Types of fluid used in the fluid-filled conduit include a liquid, a gas, or some combination in various embodiments Parasympathetic targets can be inhibited to provide a sympathetic response. According to various embodiments of the present subject matter, parasympathetic neural targets include, but are not limited to, a vagus nerve, a baroreceptor, and a cardiac fat pad.

Sympathetic targets can be inhibited to provide a parasympathetic response. According to various embodiments of the present subject matter, sympathetic neural targets include, but are not limited to, a peroneal nerve, a sympathetic column in a spinal cord, and cardiac post-ganglionic sympathetic neurons. Examples of applications of neural stimulation treatment that elicits a parasympathetic response, include, but are not limited to heart failure treatment, hypertension treatment and cardiac remodeling treatment.

Heart Failure

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

Hypertension

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac Remodeling

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients. Chronic hypertension seems to be related to hypertrophy in diastolic heart failure, whereas response to reduced cardiac output following MI to increase cardiac output via heart rate and contractility may be more relevant for systolic heart failure.

Treatments and Systems for Applying Same

The present subject matter relates to systems, devices and methods for providing thermal neuroinhibition treatment, including using thermal transfer to cool a neural target to inhibit neural traffic. Various embodiments provide a stand-alone device, either externally or internally, to provide thermal neuroinhibition treatment.

FIG. 1 illustrates a block diagram of a thermal neuroinhibition system, according to one embodiment. The system 100 includes a device 102 and a lead 104 connected to the device. In various embodiments, the device 102 is implantable. Examples of the device 102 include, but are not limited to, the device of FIG. 2. Examples of the lead 104 include, but are not limited to, the lead of FIG. 3. The device 102 includes a heat pump and a controller adapted to control the heat pump, in various embodiments. The lead 104 includes a coolant conduit along its length. The lead further includes a proximal portion 106 connected to the device 102, and a distal portion 108. An embodiment of distal portion 108 is shown in the exploded portion of the figure. In various embodiments, distal portion 108 includes an insulating layer 188 extending along the lead back to proximal portion 106, to insulate the lead. The lead may be protected by insulation that can have both thermal and electrical insulative properties. The distal portion 108 further includes an uninsulated or exposed portion of the conduit 184 (also called the cooling circuit). The distal portion 108 also includes a temperature sensor 182 to provide feedback to the device for controlling the temperature at the distal end, in one embodiment. In an embodiment, the distal portion 108 further includes electrodes 186. In varying embodiments, the electrodes may be used for sensing physiological parameters for a closed-loop feedback system, and/or for applying electrical stimulation for complementary neural treatment. In various embodiments, the distal portion 108 is placed contacting or adjacent to a neural target, in various embodiments. The device 102 controls the rate or circulation of the coolant to remove heat from the neural target and thus inhibit neural traffic, in varying embodiments.

Figure 2:
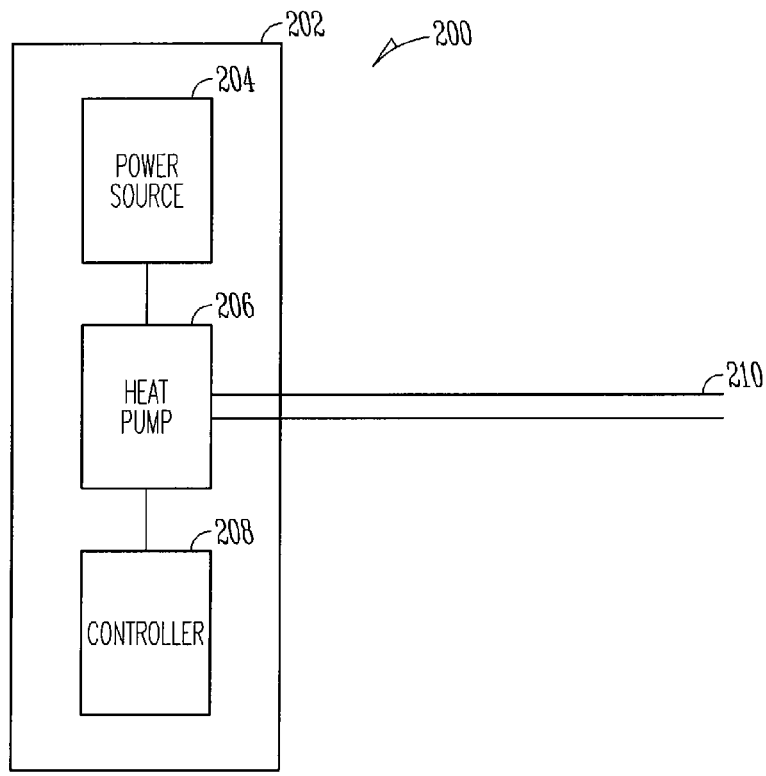
FIG. 2 illustrates a block diagram of a system for applying thermal neuroinhibition treatment, according to various embodiments.

FIG. 2 illustrates a block diagram of a system for applying thermal neuroinhibition treatment, according to various embodiments. According to one embodiment, the system 200 includes at least one implantable fluid-filled conduit 210 adapted to be placed adjacent to a neural target. The system also includes an implantable housing 202 including a power source 204, a heat pump 206 deriving power from the source and connected to the conduit, and a controller 208 within the housing. The controller 208 is connected to the heat pump 206, and is adapted to control the heat pump to effect fluid flow in the conduit 210 to cool the neural target using electromechanical refrigeration to reversibly inhibit neural activity as part of a medical treatment. The heat absorbed by the coolant is dissipated (via conduction) at the implanted device, in an embodiment. While this may result in localized heating of tissue in the vicinity of the device, the temperature increase will not be as large as the decrease at the site of cooling because the surface area of the device is much larger than the area being cooled. Normal circulation removes heat from the tissue in the vicinity of the device.

According to various embodiments, the controller 208 is adapted to control the heat pump 206 to effect fluid flow in the conduit 210 to reduce the temperature of the neural target to about 5° C. to 10° C. to inhibit nerve traffic. In an embodiment, the temperature of the neural target is reduced to about 8° C. to inhibit nerve traffic. Reduction of temperature of a nerve target below 5° C. may cause irreversible damage to the target nerve. The distal end of the conduit can be in contact with or adjacent to the neural target, in varying embodiments. One or more electrodes can be placed along the conduit, in various embodiments. The electrodes are used for sensing neural activity or stimulating the neural target, in various embodiments. In an embodiment, neural traffic is inhibited via cooling, and the electrode can electrically stimulate the target to simulate particular, arbitrary traffic. In this embodiment, the system can be used in applications for better control of motor function, for example.

In varying embodiments, the power source 204 is rechargeable. A lithium ion (Li-ion) battery is used as a power source, in an embodiment. The amount of energy required to cool water from 37° C. (approximate body temperature) to 8° C. is:

$$\Delta U = mc\Delta T = (1 \text{ g/cm}^3)*(4.186 \text{ J/g } ° \text{C.})*((37-8)° \text{C.}) = 122 \text{ J/cm}^3$$

Various rechargeable Li-ion batteries have an energy density of approximately 900 J/cm$^3$. Therefore, a system embodiment with a 30 cc Li-ion battery could perform 220 cycles of cooling 1 cc of body tissue to 8° C. before requiring recharging, if a coefficient of performance (COP) of 1.0 is assumed. Using body temperatures, the theoretical limit to cool tissue to 8° C. is COP of 9.7 (COP=281K/(310K−281K). A perfectly efficient system could therefore get as many as 2100 cycles from a 30 cc Li-ion battery. The power source is recharged from an external source using electromagnetic field transfer, in an embodiment. Other means for recharging the battery, such as from a second internal source, can be used without departing from the scope of this disclosure. In various embodiments, the power source can be external (such as via electromagnetic field transfer), or a combination of external and internal sources. Thermal neuroinhibition can be used to control sensation, control motor activity, and/or control unwanted reflexes, in various embodiments. The medical treatment that this therapy can be used for includes, but is not limited to: pain control (such as for angina, chronic joint/tendon pain, back pain, defibrillation pain), regulation of the cardiovascular system (such as heart rate regulation, atrial fibrillation, diastolic dysfunction, diastolic heart failure, elevated sympathetic nerve activity, LQTS), control of incontinence, modulation of gastrointestinal motility, and overactive bladder treatment. In various embodiments, an external device or external power source is used to provide power to cool the fluid in the conduit. The fluid can be a liquid, a gas, or a combination of liquid and gas. In one embodiment, the system also includes a sensor to provide a closed loop system. Types of sensors include, but are not limited to, temperature sensors, heart rate sensors, or neural activity sensors. A temperature sensor allows the controller to precisely control temperature of the coolant at the neural target. In one embodiment, the system inhibits nerve traffic when a sensed parameter exceeds or falls below a predetermined threshold. Examples of sensed parameters include, but are not limited to, heart rate, neural activity, changes in repolarization or premature beats.

Figure 3:
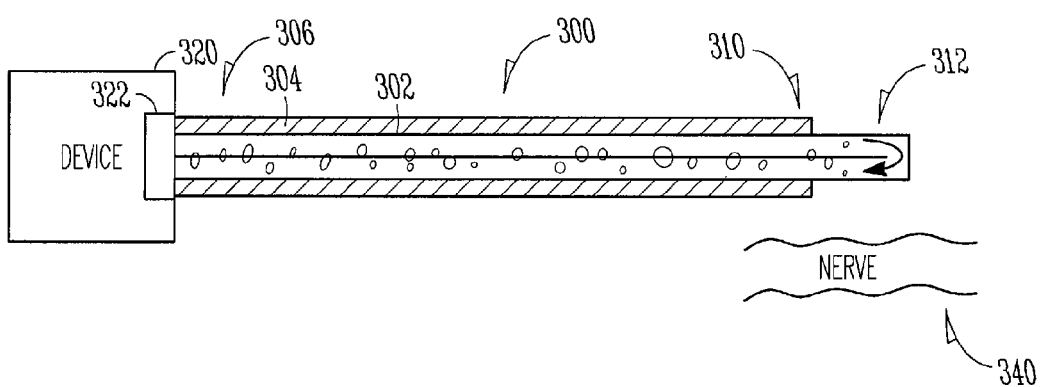
FIG. 3 illustrates a block diagram of an implantable lead for use in a thermal neuroinhibition treatment system, according to various embodiments.

FIG. 3 illustrates a block diagram of an implantable lead for use in a thermal neuroinhibition treatment system, according to various embodiments. According to one embodiment, the lead 300 includes at least one implantable fluid-filled conduit 302 along the length of the lead. Thermal insulation 304 is around at least a portion of the lead. The proximal end 306 of the lead is adapted to connect to a device 320 having at least one heat pump 322. The distal end 310 of the lead is adapted to be placed adjacent a neural target 340. The distal end 310 includes an uninsulated portion 312 of the conduit (or "cooling circuit") adapted to cool the neural target 340 using electromechanical refrigeration to reversibly inhibit neural activity as part of a medical treatment. The "cooling circuit" is a conduit that contains circulating coolant (liquid or gas). The conduit, or at least a portion thereof, is uninsulated in the vicinity of the tissue targeted to be cooled. However, the circuit is insulated between the device and the target tissue. Within the device, the circuit may be insulated or uninsulated, at least some portion of the circuit within the device is not insulated so that the heat returning from the target tissue can be extracted and dissipated.

In various embodiments, one or more sensors are included at the distal end, and the sensors are used in a closed loop feedback thermal neuroinhibition system. In an embodiment, the lead 300 also includes a temperature sensor at the distal end. The temperature sensor is adapted to provide feedback to the cooling circuit. In one embodiment, the lead 300 also includes at least one electrode at the distal end. The electrode can be used to monitor neural activity adjacent the lead, and/or to provide electrical stimulation, according to various embodiments. The distal end 310 of the lead further includes a heart rate sensor, in an embodiment. In varying embodiments, the distal end of the lead includes any one or more of a variety of physiological parameter sensors. In an embodiment, the thermal insulation is positioned around the lead to focus cooling on the neural target. The fluid in the conduit can be a liquid, a gas, or a combination of liquid and gas in various embodiments. The conduit can be in contact with or adjacent to the neural target, such that the conduit is in close proximity to the nerve. In one embodiment, the distal end of the conduit would be in a "cuff" arrangement wherein tabs along the lead are wrapped around the nerve and fastened at the free ends to hold the assembly in place.

Figure 4:
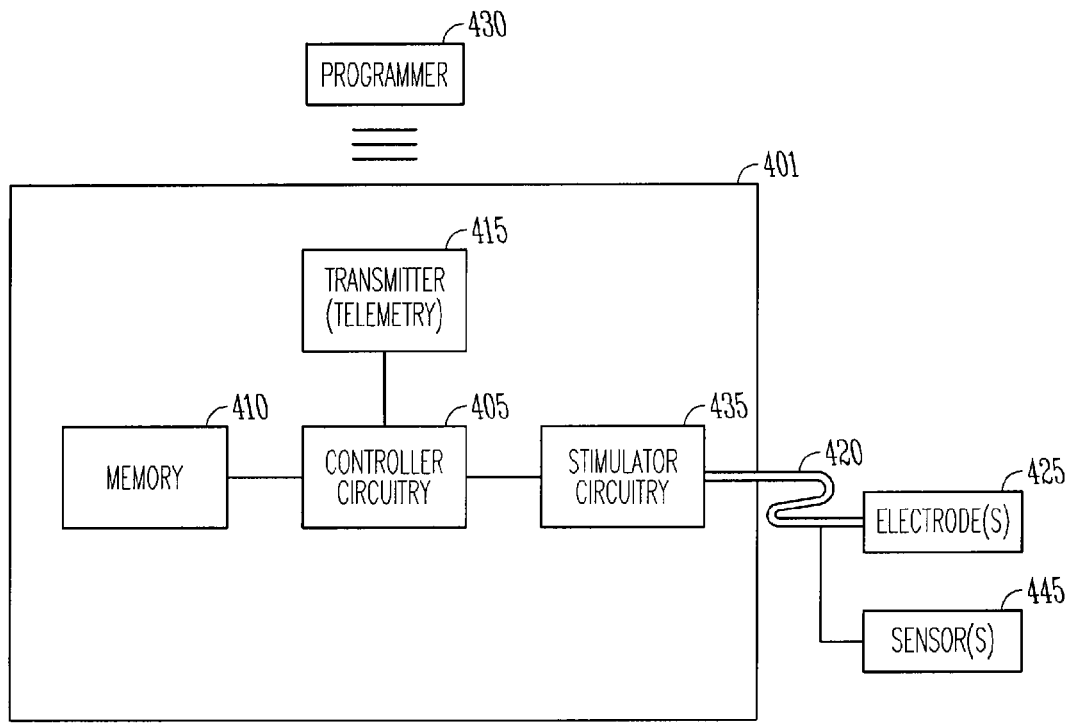
FIG. 4 illustrates a block diagram of a system with an implantable medical device (IMD), according to various embodiments.

FIG. 4 illustrates a block diagram of a system with an implantable medical device (IMD) such as the IMD illustrated in the system of FIG. 2, according to one embodiment. The system includes an IMD 401, a lead 420 (such as the lead illustrated in FIG. 3) coupled to the IMD 401, and at least one electrode 425. The IMD includes a controller circuit 405, a memory circuit 410, a telemetry circuit 415, and a stimulation circuit 435. The controller circuit 405 includes a heat pump, and is operable on instructions stored in the memory circuit to deliver thermal neuroinhibition treatment. Treatment is delivered by the stimulation circuit 435 through the lead 420, and the lead can have one or more electrode(s) 425. The telemetry circuit 415 allows communication with an external programmer 430. The programmer 430 is used to adjust the programmed treatment provided by the IMD 401, and the IMD reports device data (such as battery capacity and lead resistance) and treatment data (such as sense and stimulation data) to the programmer using radio telemetry, for example. The illustrated embodiment also includes at least one integrated sensor 445 connected to lead 420 as part of the thermal neuroinhibition treatment system.

Figure 5:
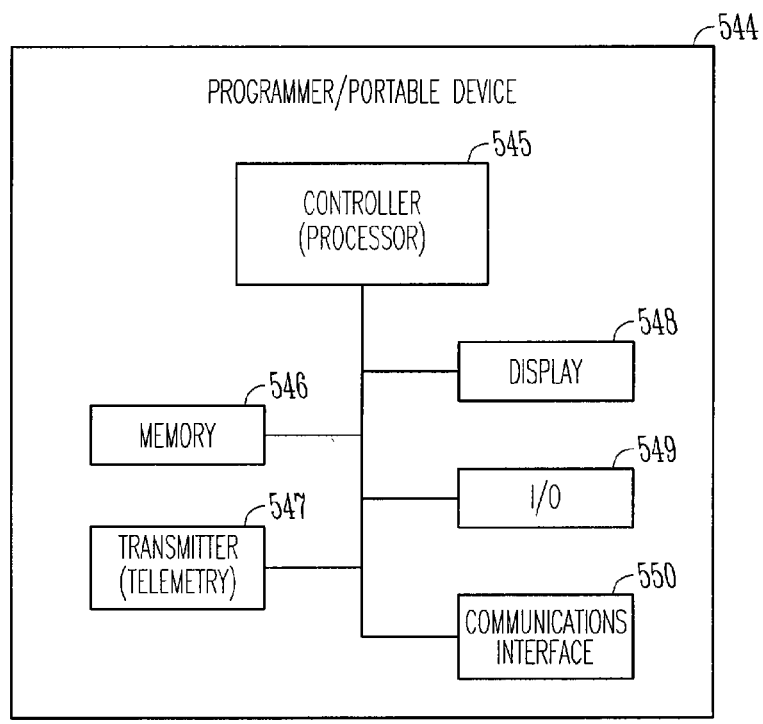
FIG. 5 illustrates a block diagram of a programmer such as illustrated in the system of FIG. 4 or other external device to communicate with the IMD(s), according to various embodiments.

FIG. 5 illustrates a block diagram of a programmer 544, such as the programmer 430 illustrated in the system of FIG. 4 or other external device to communicate with the IMD(s), according to one embodiment. Examples of other external devices include Personal Digital Assistants (PDAs), personal laptop and desktop computers in a remote patient monitoring system, or a handheld device in such a system. The illustrated programmer 544 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the devices. The illustrated programmer 544 further includes a transceiver 547 and associated circuitry for use to communicate with a device. Various embodiments have wireless communication capabilities. For example, various embodiments of the transceiver 547 and associated circuitry include a telemetry coil for use to wirelessly communicate with a device. The illustrated device 522 further includes a display 548, input/output (I/O) devices 549 such as a keyboard or mouse/pointer, and a communications interface 550 for use to communicate with other devices, such as over a communication network.

FIGS. 6A-6C illustrate a neural target for applying thermal neuroinhibition treatment, according to one embodiment. FIG. 6A illustrates a neural target area in the vicinity of a patient's neck 600. FIG. 6C illustrates an exploded view of the target area, showing the longus colli muscle 601, the middle cervical ganglion 602, the stellate ganglion 603, the scalenus anterior muscle 604, the scalenus medius muscle 605, the transverse process of the first thoracic vertebra 606, the tubercle of the first rib 607, the brachial plexus 608, and the dome of pleura 609. FIG. 6B shows the placement of a thermal neuroinhibition lead 622 adjacent the vagal nerve in the target area. The lead 622 is connected to a device 620 that controls and provides power for cooling the neural target. The device 620 can be internal or external to the body of the patient, in various embodiments.

Figure 7:
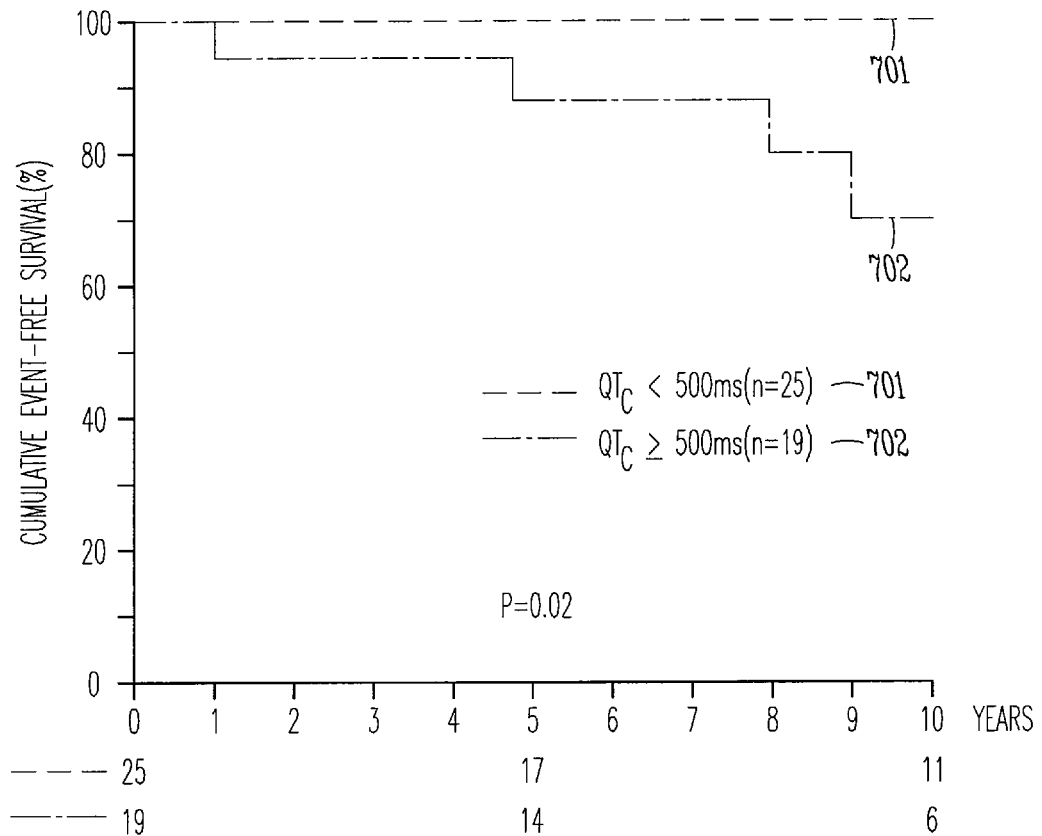
FIG. 7 illustrates a graphical diagram of an impact of sympathetic denervation treatment, according to various embodiments.

FIG. 7 illustrates a graphical diagram of an impact of sympathetic denervation therapy, according to one embodiment. One application of the discussed thermal neuroinhibition therapy is for treating patients with life-threatening ventricular arrhythmias induced by elevated sympathetic nerve activity (e.g. LQTS or Long QT Syndrome). The graph shows the cumulative event-free survival percentage for LQTS patients over time with application of sympathetic denervation. The graph shows improvement in survival (without events) for patients having therapy 701 compared to patients not having therapy 702. As discussed, thermal neuroinhibition therapy can also be adapted to treat a variety of other conditions, including but not limited to diastolic dysfunction, diastolic heart failure, atrial fibrillation, pain or incontinence.

Figure 8:
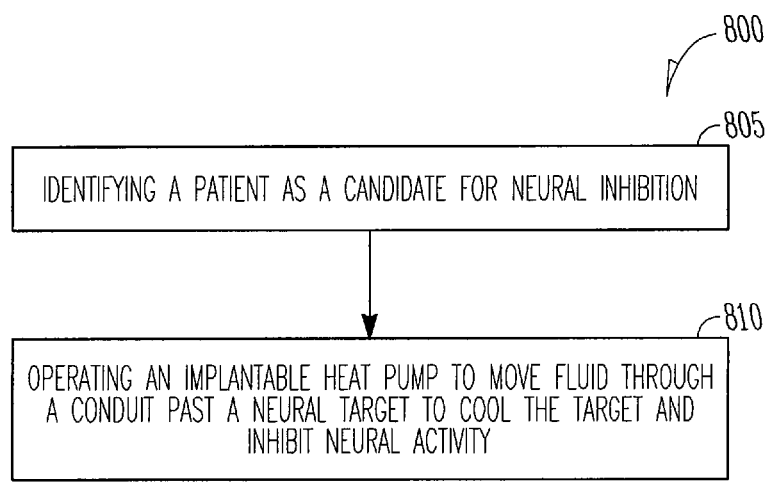
FIG. 8 illustrates a flow diagram of a method for applying thermal neuroinhibition treatment, according to various embodiments.

FIG. 8 illustrates a flow diagram of a method for applying thermal neuroinhibition treatment, according to one embodiment. According to an embodiment, the method 800 includes identifying a patient as a candidate for neural inhibition, at 805. The method also includes operating an implantable heat pump to move fluid through a conduit past a neural target to cool the target and inhibit neural activity, at 810. In various embodiments, the method also includes sensing a physiological parameter and adjusting the cooling of the neural target based on the sensed physiological parameter. Examples of physiological parameters sensed for a closed-loop system include, but are not limited to, heart rate, temperature and neural activity.

According to various embodiments, sensing a physiological parameter includes sensing sympathetic neural activity, and adjusting the cooling of the neural target includes inhibiting nerve traffic when neural activity exceeds a predetermined threshold. According to an embodiment, sensing a physiological parameter includes sensing heart rate, and adjusting the cooling of the neural target includes inhibiting nerve traffic when heart rate exceeds a predetermined threshold. Nerve traffic can also be inhibited based on changes in repolarization or premature beats, in various embodiments. According to various embodiments, neuroinhibition therapy can be combined with other implantable device functions (such as electrical, chemical or mechanical treatment) to provide treatment. For example, sympathetic activity can be regulated using thermal neuroinhibition in conjunction with rate adaptive pacing to provide a physiologically appropriate response when a patient becomes active. Thus, more sympathetic activity is allowed to regulate heart rate, contractility, and blood pressure when activity is sensed.

The method can be used to impact incontinence or overactive bladder by interrupting nerve traffic that causes sphincter relaxation and/or contraction of muscles involved in urinary or fecal voiding, in an embodiment. In one embodiment, the method is used to treat atrial tachyarrhythmia. For example, prior to shock delivery, the system activates to numb nerves and blunt pain associated with the shock. Cardiac nerves and/or fat pads can be selectively inhibited for this treatment. The system embodiment for atrial cardioversion uses an entirely implantable system with self-contained power and may use a rechargeable battery. In another embodiment, the method is used to treat occasional joint pain. In that case, the patient triggers occasional therapy as needed to manage pain. The system embodiment for local pain relief can be totally or partially implantable, deriving power from an internal source or one external the body, via electromagnetic field transfer, for example, or from a combination of energy sources.

Although specific embodiments have been illustrated and described herein, it will be appreciated by those of ordinary skill in the art that any arrangement which is calculated to achieve the same purpose may be substituted for the specific embodiment shown. It is to be understood that the above description is intended to be illustrative, and not restrictive. The scope of the present subject matter should be determined with reference to the appended claims, along with the full scope of equivalents to which such claims are entitled.

We claim:

1. A system, comprising:
an electrical lead including at least one implantable fluid-filled conduit along a length of the lead, the conduit adapted to be placed adjacent to a neural target; and
an implantable housing including:
a power source;
a stimulation circuit connected to the electrical lead, the stimulation circuit adapted to provide electrical stimulation to the neural target;
a heat pump deriving power from the source, the heat pump connected to the conduit; and
a controller connected to the heat pump, the controller adapted to control the heat pump to effect fluid flow in the conduit to cool the neural target using electromechanical refrigeration to reversibly inhibit neural activity as part of a medical treatment.

2. The system of claim 1, wherein the controller is adapted to control the heat pump to effect fluid flow in the conduit to reduce the temperature of the neural target to about 5° C. to 10° C. to inhibit nerve traffic.

3. The system of claim 2, wherein the controller is adapted to control the heat pump to effect fluid flow in the conduit to reduce the temperature of the neural target to about 8° C. to inhibit nerve traffic.

4. The system of claim 1, further comprising at least one electrode along the implantable fluid-filled conduit.

5. The system of claim 4, wherein the electrode is adapted to stimulate the neural target.

6. The system of claim 4, wherein the electrode is adapted to sense neural activity.

7. The system of claim 1, wherein the power source is rechargeable.

8. The system of claim 1, wherein the power source includes a Lithium ion battery.

9. The system of claim 1, wherein the power source includes a battery having an energy density of about 900 J/cm$^3$.

10. The system of claim 1, wherein the medical treatment includes at least one of pain control, regulation of the cardiovascular system, control of incontinence, modulation of gastrointestinal motility, and overactive bladder treatment.

11. An electrical lead for use in a local neural refrigeration system, the lead comprising:
at least one implantable fluid-filled conduit along the length of the lead;
thermal insulation around at least a portion of the lead,
a proximal end adapted to connect to a device having at least one heat pump; and
a distal end adapted to be placed adjacent a neural target, the distal end including an uninsulated portion of the conduit adapted to cool the neural target using electromechanical refrigeration to reversibly inhibit neural activity as part of a medical treatment.

12. The lead of claim 11, further comprising:
a temperature sensor at the distal end, the temperature sensor adapted to provide feedback to the cooling circuit.

13. The lead of claim 11, further comprising:
at least one electrode at the distal end.

14. The lead of claim 13, wherein the electrode is adapted to monitor neural activity adjacent the lead.

15. The lead of claim 11, wherein the thermal insulation is positioned around the lead to focus cooling on the neural target.

16. The lead of claim 11, wherein the distal end further comprises a heart rate sensor.

17. The lead of claim 11, wherein the distal end further comprises a neural activity sensor.

18. The lead of claim 11, wherein the fluid in the implantable fluid-filled conduit includes a liquid.

19. The lead of claim 11, wherein the fluid in the implantable fluid-filled conduit includes a gas.

* * * * *